(12) United States Patent
Hoag (10) Patent No.: US 7,976,508 B2
(45) Date of Patent: Jul. 12, 2011

(54) MEDICATION SAFETY SYSTEM FEATURING A MULTIPLEXED RFID INTERROGATOR PANEL

(75) Inventor: Robert E. Hoag, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 1127 days.

(21) Appl. No.: 11/431,771

(22) Filed: May 10, 2006

(65) Prior Publication Data

US 2006/0265246 A1    Nov. 23, 2006

Related U.S. Application Data (60) Provisional application No. 60/679,347, filed on May 10, 2005.

(51) Int. Cl.
*A61M 3/00* (2006.01)
*A61M 31/00* (2006.01)
*G08B 13/14* (2006.01)

(52) U.S. Cl. .............. 604/189; 604/65; 604/66; 604/67; 340/572.1

(58) Field of Classification Search ................... 604/189, 604/67; 705/2, 3
See application file for complete search history.

(56) References Cited

U.S. PATENT DOCUMENTS

| | | | |
|---|---|---|---|
| 4,194,637 A * | 3/1980 | Edson | 211/96 |
| 4,551,133 A | 11/1985 | Zegers De Beyl et al. | |
| 5,018,388 A | 5/1991 | Mosebach et al. | |
| 5,899,665 A * | 5/1999 | Makino et al. | 417/20 |
| 6,380,858 B1 | 4/2002 | Yarin et al. | |
| 7,232,423 B2 * | 6/2007 | Mernoe | 604/135 |
| 7,356,382 B2 * | 4/2008 | Vanderveen | 700/282 |

(Continued)

FOREIGN PATENT DOCUMENTS

EP    0 328 163 A2    8/1989

(Continued)

OTHER PUBLICATIONS

International Search Report—International Application No. PCT/US2006/018025; International Filing Date: May 10, 2006.

*Primary Examiner* — Nicholas D Lucchesi
*Assistant Examiner* — Ian K Holloway
(74) *Attorney, Agent, or Firm* — McDermott, Will & Emery (57) ABSTRACT

A medication safety system includes a panel mounted to an IV pole above a multi-channel infusion pump also mounted to the IV pole. The panel includes multiple RFID readers for reading the RFID tags placed on each of the medication containers mounted to the panel. The pump includes a controller that communicates with the RFID readers at the panel to receive the information read by the RFID readers and automatically program the respective pump channel. A verification program verifies that the medication delivery information from the containers matches the patient identified for the pump and the programming parameters of the pump fall within acceptable ranges. In another aspect, the panel contains multiple vibration devices to impart vibrations to the medication of each of the containers mounted to the panel. Those vibrations are sensed by the particular pumping channel to confirm that the correct channel has been programmed for that medication. When the clinician opens the door of the pumping channel, the pump may request information from the RFID reader at the panel for that medication and may wait for receipt of the vibrations in the medication of the tubing mounted into the channel.

35 Claims, 5 Drawing Sheets

U.S. PATENT DOCUMENTS

| | | |
|---|---|---|
| 2002/0032435 A1 | 3/2002 | Levin |
| 2002/0038392 A1 | 3/2002 | De La Huerga |
| 2002/0143320 A1 | 10/2002 | Levin |
| 2002/0188259 A1 | 12/2002 | Hickle et al. |
| 2003/0074223 A1 | 4/2003 | Hickle et al. |
| 2003/0135388 A1* | 7/2003 | Martucci et al. .................. 705/2 |
| 2003/0183226 A1 | 10/2003 | Brand et al. |
| 2003/0183683 A1 | 10/2003 | Stewart |
| 2003/0233069 A1 | 12/2003 | Gillespie, Jr. et al. |
| 2004/0051368 A1 | 3/2004 | Caputo et al. |
| 2004/0104271 A1 | 6/2004 | Martucci et al. |
| 2004/0121767 A1 | 6/2004 | Simpson et al. |
| 2004/0128162 A1 | 7/2004 | Schlotterbeck et al. |
| 2004/0150525 A1 | 8/2004 | Wilson et al. |
| 2004/0176667 A1* | 9/2004 | Mihai et al. .................. 600/300 |
| 2004/0193453 A1* | 9/2004 | Butterfield et al. ................ 705/2 |
| 2005/0209547 A1* | 9/2005 | Burbank et al. ............. 604/5.01 |
| 2005/0277911 A1* | 12/2005 | Stewart et al. ............. 604/890.1 |
| 2006/0206356 A1* | 9/2006 | Vanderveen ...................... 705/2 |
| 2007/0154370 A1* | 7/2007 | Mehus et al. ................. 422/257 |

FOREIGN PATENT DOCUMENTS

| | | |
|---|---|---|
| EP | 0 394 973 A1 | 10/1990 |
| WO | WO 91/00113 | 1/1991 |
| WO | WO 03/094075 A1 | 11/2003 |
| WO | WO 03/098534 A1 | 11/2003 |
| WO | WO 2004/088567 A2 | 10/2004 |
| WO | WO 2005/118054 A1 | 12/2005 |
| WO | WO 2006/086701 A1 | 8/2006 |

* cited by examiner

MEDICATION SAFETY SYSTEM FEATURING A MULTIPLEXED RFID INTERROGATOR PANEL

CROSS-REFERENCES TO RELATED APPLICATIONS

This application claims the benefit of U.S. Provisional Application No. 60/679,347, filed May 10, 2005.

BACKGROUND OF THE INVENTION

The present invention relates generally to programming medical devices, and more particularly, to a system and a method for automatically verifying the medication to be infused into the patient.

Physicians and other medical personnel apply intravenous ("IV") infusion therapy to treat various medical complications in patients. IV infusion therapy typically involves infusing medical fluids, such as drugs or nutrients, from a fluid supply, such as a bag, bottle, or other container, through the tube, or conduit, of a fluid administration set ("IV set") to a cannula inserted into a patient's blood vessel. In a typical healthcare facility, a physician enters an order for medication for a particular patient. This order may be handled either as a simple prescription slip, or it may be entered into an automated system, such as a physician order entry ("POE") system. The prescription slip or the electronic prescription from the POE system is routed to the pharmacy, where the order is filled. Typically, the prescribed medication is prepared by a pharmacist and added to a bag or bottle at a pharmacy. Under the supervision of a pharmacist the contents of the bag is identified with text on a paper label that is attached to the bag. This label may identify the contents of the bag by other means, such as a bar code, magnetic device or by use of a radio frequency (RF) signal interactive device such as an RFID tag, as examples. The prepared medication is then delivered to a nurse's station for subsequent administration to the patient.

For safety reasons and in order to achieve optimal results, the medical fluid is often administered in accurate amounts as prescribed by the doctor and in a controlled fashion by using an infusion pump. Infusion pumps operate by displacing the fluid from a fluid administration set to force fluid from the fluid supply through the tube and into the patient. The infusion pump is programmed by an operator such as a nurse or other medical personnel, with operating parameters to achieve the administration of the drug as prescribed by the physician. Such operating, or pumping, parameters are drug and patient specific. That is, the pumping parameters are selected based on the particular drug prescribed and the specific patient for whom they are intended. It is the nurse's responsibility to match the prescribed drug with the correct patient and with the properly programmed pump.

Healthcare facilities are concerned with providing safe medication systems in an era of nursing shortages and continually strive to provide quality patient care. Medical errors, such as when a patient receives the wrong drug or receives the correct drug at the wrong time or in the wrong dosage, are significant concerns for all health care facilities. In the administration of medication, focus is typically directed to the following five "rights" or factors: the right patient, the right drug, the right route, the right amount, and the right time. The nurse aims to ensure that these "rights" are all accomplished. Systems and methods seeking to reduce medical errors should also take these five rights into consideration.

Medical infusion pumps have advanced greatly over the years and permit more precise infusion control resulting in much better treatment for patients. Doctors are more assured that the doses and infusion rates that they prescribe for their patients can be delivered to the patients accurately by infusion pumps. The administration may be conducted in small discrete doses or may be given at an essentially continuous rate. Infusion pump therapy may be electronically controlled to deliver precise, metered doses at exactly determined levels, thereby providing a beneficial gradual infusion of medication to the patient. In this manner, the infusion pump is able to mimic the natural process whereby desired chemical balances are maintained precisely by operating on a continuous time basis. However, there remains a continuing concern that the right drug is matched to the right pump.

Certain manufacturers have created bar code systems designed to reduce the risk of intravenous medication errors by automatically programming the infusion system in an effort to increase the chances that the right drug goes to the right patient through the right pump. Such systems seek to eliminate the scenario of errors caused by clinicians incorrectly programming a pump by providing a system that automatically reads programming instructions and automatically programs the pump in accordance with those instructions. While some such systems can provide a significant benefit, others can involve considerable effort by the clinician to:

scan the bar code of the patient's identification device;
    scan the bar code of the clinician's badge;
    scan the bar code of the infusion system; and
    scan the bar code of the IV medication container label;
sometimes multiple times.

A system is desired that accomplishes the objectives of a bedside bar code system but is more automated and requires less scanning of multiple bar codes. Those skilled in the art have recognized a need for a system that reduces the amount of time it takes to set up an infusion, and also provides the safety features that are the objectives of a bar code system. Unfortunately, some skill is required with a bar code system when it is working properly and when it is not working, information must be manually input to the appropriate medical devices by the clinician, with the attendant risk of typing or entry errors. Even when the bar code system is working properly, a clinician can mistakenly scan the label of another device that is in close proximity to the label he or she desires to scan, especially when the bar code scanner has a wide scan beam. When the bar code labels become wet with medical fluids, or are otherwise obscured due to one reason or another, they sometimes become unreadable by the bar code scanner then requiring the manual input of their information with its attendant risk of incorrect data entry.

There is the further problem of multiple fluid conduits where multi-channel pumps are involved. The same can occur where single-channel pumps are involved but many are mounted in close proximity to each other.

In some cases, a single patient may be prescribed multiple simultaneous infusions for different drugs, sometimes four or more, which requires multiple infusion pumps that may all be programmed differently. In such cases, there will also be multiple IV administration sets each with its own fluid conduit to be connected with the patient. Where there are multiple infusion conduits present, there is a concern that a fluid conduit may be mounted to the wrong infusion pump channel or wrong infusion pump and the drug delivered under incorrect pumping parameters. As an example, where multiple infusion pump channels are located side by side, there is a concern that a fluid infusion line or conduit may be installed in the wrong pump channel. Where a more dense infusion pump environment exists, it is important to be sure that the correct medical fluid conduits are being mounted to the correct pump or "channel." The fluid sources for all pump channels may be suspended immediately above the pump channels and the conduits of the administration sets may become intertwined, thus making it more difficult to select the correct conduit for the particular channel of the pump.

Prior attempts have been made to assure that the right drug is administered to the right patient through the right pump. In one example, a bar code label identifying the drug and patient is applied to the bag at the pharmacy. After an operator such as a nurse manually programs the pump, a bar code scanner connected to the pump is used to read the bar code label on the bag to verify that it identifies the same medication as that programmed into the pump. In another example, U.S. Pat. No. 5,078,683 to Sancoff et al. discloses a bar code label applied to the bag that is read with a bar code scanner to automatically program the pump, thus avoiding manual programming entirely.

Even though the foregoing have provided significant advances in the art to avoid medication errors and have reduced the likelihood of such medication errors, there still exists some risk that an incorrect bag may become mounted to a pump or pump channel. Stated differently, there still exists some risk that a bag may become connected to the wrong pump or pump channel. For example, the nurse could possibly scan the bar code label of the correct bag, but become distracted and mount the conduit of the administration set connected to the bag to the wrong pump channel. Even if the nurse does not become distracted, the various fluid conduits in a multiple fluid infusion may be difficult to distinguish from one another and tracing the fluid conduit associated with the right bag may become burdensome, especially where the fluid conduits have become tangled with each other. In such a case, the nurse may inadvertently choose the wrong fluid conduit to install in the pump even after identifying the correct fluid supply.

Hence, those skilled in the art have recognized that a need still exists for a system and method to more accurately ensure that the correct fluids are infused into the patient at the correct pumping parameters. Further, those skilled in the art have recognized a need for a system and method that can more reliably determine that the correct fluid source is connected to the correct infusion pump or pump channel so that the fluid is infused into the patient in accordance with the correct pumping parameters. Additionally, those skilled in the art have recognized a need for a system that accomplishes the objectives of a bedside bar code system without taxing the clinician with the scanning of multiple bar codes. A need has also been recognized for a more automated system that provides for automatic infusion setup with the clinician only needing to verify the setup and then pressing the START key to begin infusion. A need has been recognized for providing accurate medical information to the correct device without the need for manually scanning labels or manually inputting information, yet is reliable and is cost effective to use. The present invention fulfills these needs and others.

SUMMARY OF THE INVENTION

Briefly and in general terms, the present invention is directed to a system and method for wirelessly, non-optically, reading medication information and a pumping parameter from a medication container at a panel located above the medication delivery apparatus and for verifying that the correct medication is mounted to the correct delivery apparatus.

In one aspect, there is provided a medication safety system for reading medication delivery information from an information device located at a medication container and providing that medication delivery information to a medication delivery apparatus, the system comprising a panel at which the medication container having the information device is mounted, a conduit connected to the medication container configured to conduct the medication of the container to the medication delivery apparatus, a reader located at the panel configured to wirelessly read the information device and to provide an information signal representative of the information contained in the information device, and a controller located at the medication delivery apparatus configured to receive the information signal and to configure the medication delivery apparatus in accordance with the information signal. In a detailed aspect, the information device comprises patient identification information and an infusion pump programming parameter, and the controller is further adapted to compare the patient identification information to information from a patient to which the medication delivery apparatus has been identified, and to automatically program the mediation delivery apparatus with the pump programming parameter. In another detailed aspect, the controller is configured to receive the information signal wirelessly, and in one aspect, the wireless reader comprises an RFID interrogator that reads the information device on the medication container.

In yet further aspects in accordance with the invention, the panel comprises multiple locations at which a plurality of medication containers may be mounted, each container having a conduit configured to conduct the medication of the respective container to the medication delivery apparatus and each container having an information device providing medication delivery information and patient identification information, and at least one wireless information reader device located at the panel so as to read information contained in each of the information devices mounted at the panel. In more detailed aspect, the medication safety system further comprises a multiplexing device that provides multiplexed multiple information signals representative of the information contained in each of the information devices. In another aspect, the medication safety system comprises a plurality of wireless information reader devices located at the panel so as to read information contained in respective information devices mounted at the panel adjacent the respective reader device, with the information reader devices comprising RFID readers.

In other more detailed aspects, the controller compares the patient identification information for each of the containers to a patient identified to the pump and if the identifications do not match, the controller provides an alert. The system further comprises a delivery parameter verification system in which the delivery parameter read from the information device is compared to a data base having an acceptable range for the delivery parameter and if the delivery parameter contained in the information signal is outside the acceptable range, the verification system will provide an alert. The acceptable range of the data base comprises a hard limit and a soft limit, the verification system disabling the pump from operation if the delivery parameter from the information signal exceeds the hard limit and not disabling the pump from operation but providing an alert if the delivery parameter from the information signal exceeds the soft limit but does not equal or exceed the hard limit. In another detailed aspect, the verification system is located within the controller and in another aspect, the verification system is located at a location remote from the controller.

In other aspects, the medication safety system further comprises a patient identification reader configured to wirelessly read identification information of a patient and communicate the patient identification information to the controller. Also provided is a clinician identification reader configured to wirelessly read identification information of a clinician and communicate the clinician identification information to the controller.

In another aspect, the medication safety system further comprises an IV pole to which the panel is mounted and to which the medication delivery apparatus and controller are mounted, and a receiver mounted at the pole adjacent the controller, the receiver configured to conduct information signals from the medication reader to the controller.

In yet a further aspect, the panel further comprises a vibration device located at the position at which the container is mounted, the vibration device configured to impart vibrations to the medication of the container, the medication delivery apparatus comprising a vibration sensor configured to detect vibrations in the medication of the conduit mounted to the delivery apparatus and configured to provide a vibration signal to the controller when vibrations are sensed, and the controller further configured to provide an alert if it does not receive the vibration signal when the information device of the same medication container is read by the panel. In detailed aspects, the vibration sensor comprises a pressure transducer coupled to the conduit at an upstream portion of the delivery apparatus and adapted to convert changes in pressure in the medication of the conduit to an electrical signal.

In accordance with method aspects, there is provided a medication safety method for reading medication delivery information from an information device located at a medication container and providing that medication delivery information to a medication delivery apparatus, the method comprising mounting the medication container having the information device to a panel disposed above the medication delivery apparatus, wirelessly reading the information device with a reader mounted in the panel and providing an information signal representative of the information contained in the information device, and receiving the information signal and configuring the medication delivery apparatus in accordance with the information signal.

In accordance with further method aspects, there are provided reading patient identification information and an infusion pump programming parameter from the information device, comparing the patient identification information from the information device to information from a patient to which the medication delivery apparatus has been identified, and automatically programming the medication delivery apparatus with the pump programming parameter. Further aspects include receiving the information signal and configuring the medication delivery apparatus in accordance with the information signal wirelessly. The step of wirelessly reading the information device is performed with RF energy.

Yet additional detailed aspects include mounting multiple medication containers to the panel, each medication container having a respective information device, and wirelessly reading each of the information devices with at least one reader mounted in the panel and providing information signals representative of the information contained in each of the information devices. Another aspect comprises multiplexing the multiple information signals representative of the information contained in each of the information devices. Further, the medication safety method comprises wirelessly reading each of the plurality of information devices with multiple readers mounted in the panel and providing a plurality of information signals representative of the information contained in each of the information devices, and multiplexing the multiple information signals representative of the information contained in each of the information devices.

In further detailed method aspects, the medication safety method further comprises comparing the patient identification information for each of the containers to a patient identified to the pump, and if the identifications do not match, providing an alert. Further, the medication safety method comprises comparing the delivery parameter read from the information device to a data base having an acceptable range for the delivery parameter, and if the delivery parameter contained in the information signal is outside the acceptable range, providing an alert. In further detail, the step of comparing further includes comparing the delivery parameter read from the information device to a data base having an acceptable range in which there is a hard limit and a soft limit, disabling the operation of the pump if the delivery parameter from the information signal exceeds the hard limit, and providing an alert if the delivery parameter from the information signal exceeds the soft limit but does not equal or exceed the hard limit and not disabling the pump from operation. In one aspect, the comparing step is performed at a controller of the medication delivery apparatus, and in another, the comparing step is performed at a location remote from the medication delivery apparatus.

Other aspects and advantages of the invention will become apparent from the following detailed description and the accompanying drawings, illustrating by way of example the features of the invention.

BRIEF DESCRIPTION OF THE DRAWINGS

FIG. 4 is a front view of a medication system in accordance with aspects of the invention in which the panel shown in FIGS. 2 and 3 is located on a pole above a multi-channel infusion system, the panel having wireless RFID sensors and vibration devices as described and shown in more detail previously, the RFID sensors and vibration devices being in connection with a passive antenna mounted to the pole between the infusion system and the panel but more closely to the infusion system, the infusion system having a controller with an RFID interrogator and power transmitter to activate the RFID readers and vibration devices on the panel through the passive antenna so that the readers can read the information devices (RFID tags) on the containers and activate the vibration devices to send vibration energy through the respective conduit to a vibration sensor in a channel of the infusion system;

DETAILED DESCRIPTION OF THE PREFERRED EMBODIMENTS

Figure 1:
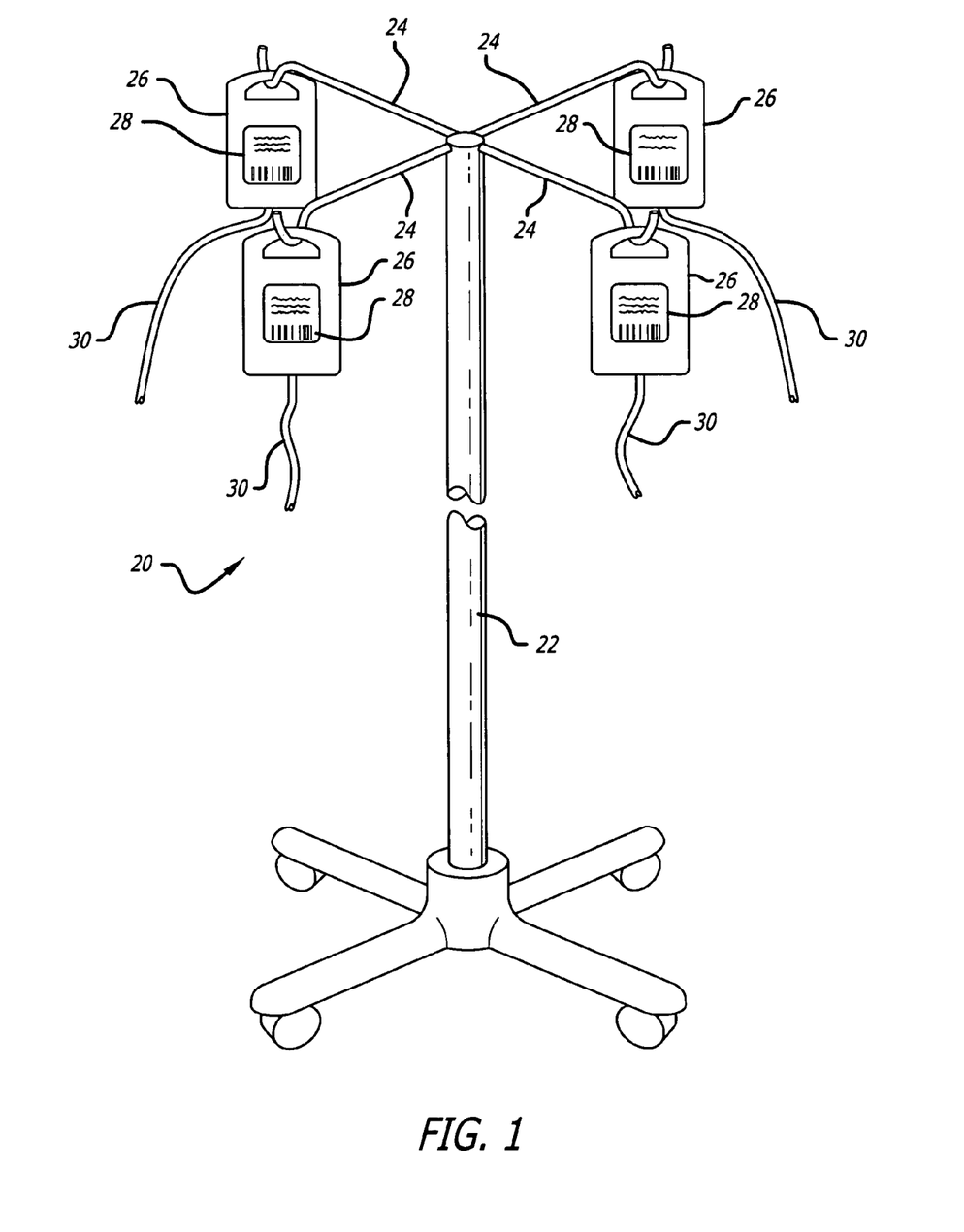
FIG. 1 is a diagram of a typical "coat hanger" pole device for mounting medication bags for infusion to a patient, showing four medication bags with four IV infusion administration sets.

Referring now in more detail to the drawings in which like reference numerals refer to like or corresponding elements among the several views, there is shown in FIG. 1 an intravenous ("IV") medication fluid container mounting pole device 20 commonly described as a "coat rack." The device includes a vertical pole 22 with multiple hanger branches 24 at the top from which articles may be hung. In this case, medication containers 26 would be hung from the hanger branches, the contents of which would be infused to a patient or patients through gravity or with other means such as a volumetric infusion pump (not shown). The pump and patient would be lower than the bags of medication. In using the coat rack with prior systems, information devices 28 on the medication containers would be scanned by a bar code scanner either before the bag is hung on the coat rack or after. This requirement for scanning can cause the problems discussed in the background section to arise. For example, a bar code scanner with a wide beam could possibly read the bar code of another container instead of the one it is meant to read.

Each fluid container 26 includes a conduit 30 or IV administration set for conducting the medication contained in the container to a patient. The conduit is typically formed of resilient tubing and may have components such as flow clamps, injection ports, and other devices formed as part of it along its length. It may also have a segment specifically designed to work with the peristaltic mechanism of an infusion pump so that the fluid may be accurately and reliably moved from the container to a patient. It will also be noted that there are four conduits hanging from the four containers. It is likely that each container has a different medication and each may require delivery at a different rate to a patient. It is therefore important to be sure that the correct conduit is mounted to the correct pump or correct channel of a multi-channel pump. A plurality of conduits such as that shown in FIG. 1 can result in medication errors where the wrong conduit is mounted to the wrong pump channel.

Figure 2:
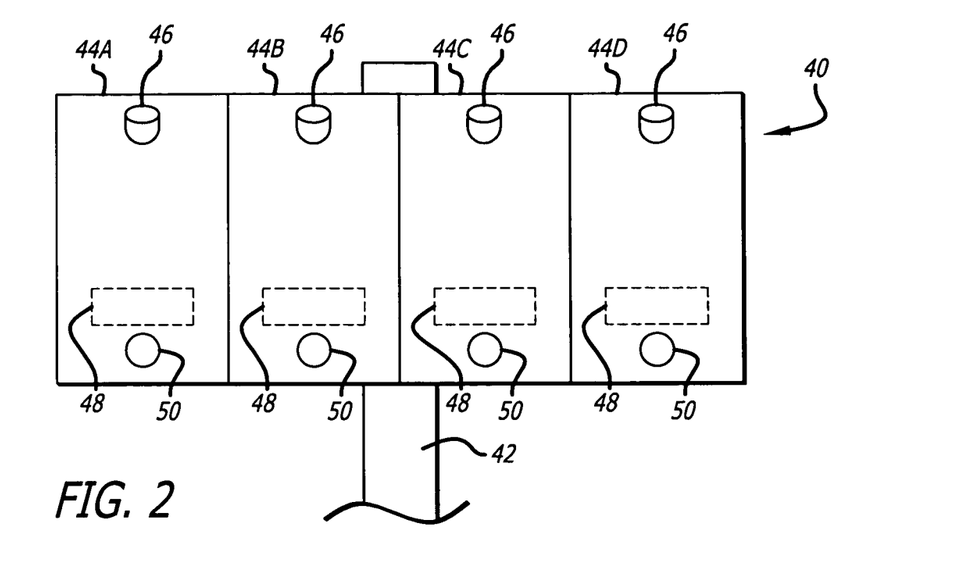
FIG. 2 is a diagram of a panel device in accordance with aspects of the invention replacing the coat hanger pole device in FIG. 1, the panel device having, in this embodiment, a plurality of wireless RFID readers and vibration devices embedded into the panel for reading information devices contained on medication containers mounted to the panel and for selectively imparting mechanical vibration energy to the contents of the containers.
Figure 3:
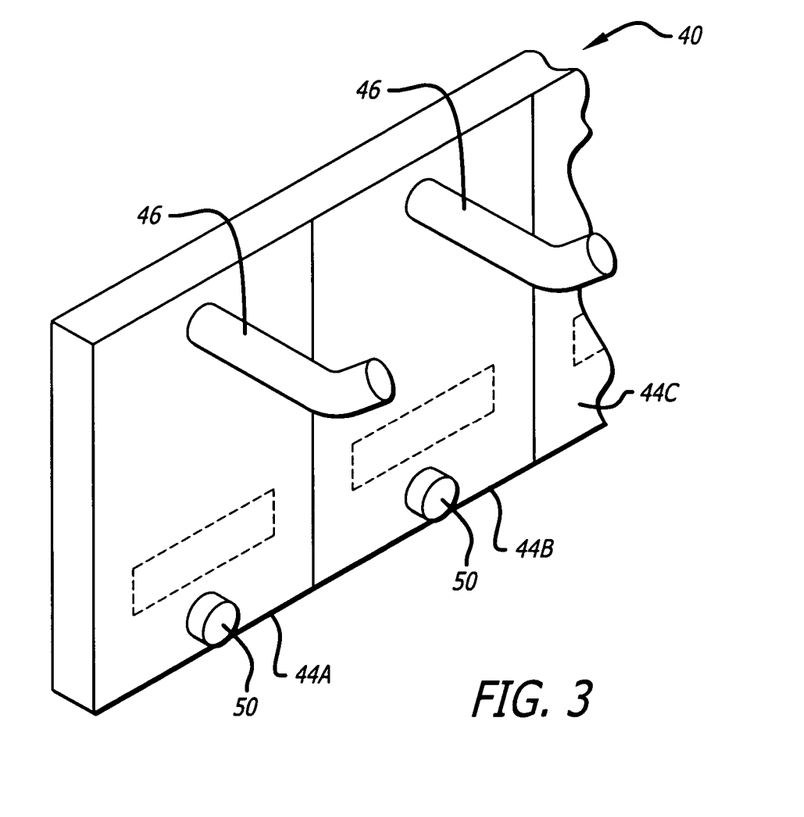
FIG. 3 is a perspective, cutaway view of the panel of FIG. 2 more clearly showing the mounting hooks for the medication containers.

Turning now to FIGS. 2 and 3, a panel 40 is attached to an IV pole 42 (FIG. 2) and serves as a replacement for the "coat rack" 20 (FIG. 1) that is typically used to hang IV infusion containers above a pump system and patient (not shown). The panel in one embodiment has four segments 44A, 44B, 44C, and 44D, each of which comprises a hanger 46, an RFID reader 48, and a vibration device 50 or vibrator. An RFID reader is also known as an RFID interrogator and includes at least one antenna used to read or interrogate an RFID tag. Such RFID tags may be passive or may be configured to be writable, that is, to store new data communicated to them by an RFID reader. RFID tags, either passive or writable, may be placed on medication containers. As an example, an RFID tag placed on a medication container may have relevant information concerning not only the medication in the container, but may also identify the patient name; patient location; patient weight, sex, age; drug; concentration; dose rate; and possibly other information. In one case, the RFID tag on the medication container may include an entire set of pumping or operational parameters so that the infusion pump may be entirely configured automatically by reading the RFID tag.

Figure 4:
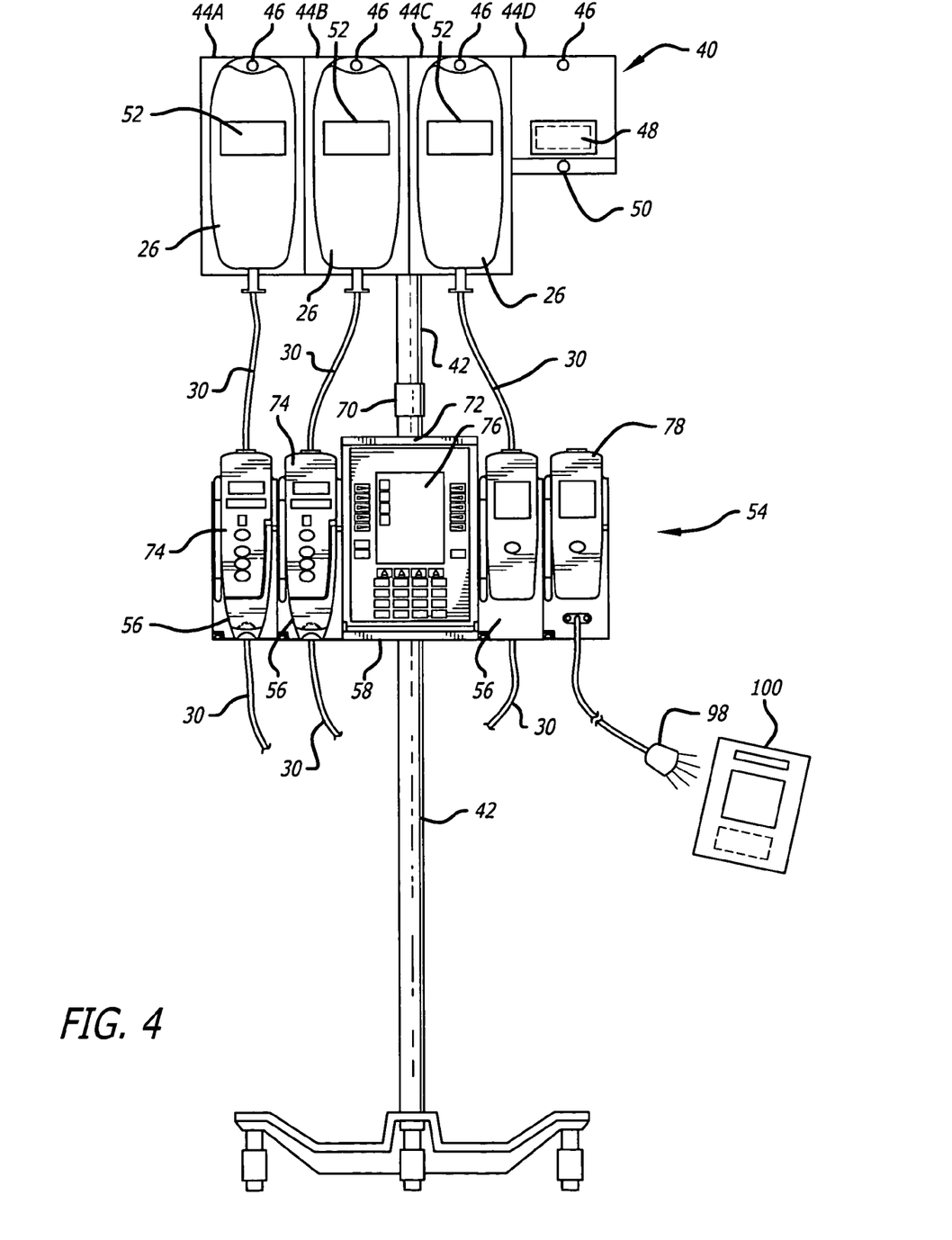

In the view shown in FIG. 4, the IV bags 26 are in fact labeled with an RFID tag or label (transponder) 52. In one embodiment, the pharmacy of the healthcare facility prepares and attaches the RFID tag to the container. Other methods of preparing and attaching the RFID tag are possible. Preparation of the RFID tag involves programming it with the necessary information, as discussed above. In one embodiment, empty containers may be received by the pharmacy with RFID tags already mounted to the container in a specific location so that the panel 40 RFID reader can be very low power and expect the RFID tag to be located on the container in the specific location. In this embodiment, the chances that the RFID reader will inadvertently read the RFID tag of a neighboring bag are eliminated. Either before the container is filled or once the container is filled with the appropriate medication, the RFID tag on the container may then be programmed with the correct information and shipped to the patient location. The pharmacy may program the RFID tag on the container or another entity may perform the programming.

When the clinician hangs one of these IV bags 26 having a programmed RFID tag 52 at the panel 40, the RFID reader 48 of the panel is able to read the RFID tag and obtain the information contained therein. This then involves an RFID reader that is closely located to the target RFID tag on the medication container 26 and having a restricted read range so that the chances of the RFID reader inadvertently reading a neighboring non-target tag are eliminated. Use of the panel with multiple RFID readers to hang multiple IV solutions involves a way of reading their RFID labels or tags without the use of a hand scanner that may inadvertently read a different tag and in any case, require the time and manual effort of clinicians. This panel approach also includes the ability to identify the correct channel of the multi-channel medication delivery apparatus or infusion system 54 for the infusion, thereby eliminating infusion conduit cross-over errors.

RFID readers and vibration devices require power to operate. Fortunately, newer devices require far less power due to increases in efficiencies of their operation. In any case, an RFID reader needs enough power to successfully interrogate an RFID tag on the medication container to obtain the information present in that tag and a vibration device needs enough power to impart vibrations into the medication having enough strength to reach an upstream pressure sensor on an infusion pump 52. The upstream pressure sensor is located downstream from the vibration device and is so named because it is located upstream from the pump mechanism of the infusion pump. To provide such power, different possibilities exist. The panel 40 itself may be connected in some way to a power source or the devices 48 and 50 may be self-powered. This could possibly be accomplished in several ways, some of which are:

1. The panel may be hard-wired with a plug into an infusion pump or controller 58 of an infusion pump;
2. Blue Tooth technology may be used. The controller 58 of the infusion pump 56 could communicate with the panel 40 by way of Blue Tooth communication.
3. A passive receiver 70 attached to the IV pole 42 in proximity to the controller 58 could carry a wireless signal sent by the controller to the panel 40. The signal could be conducted through the metal of the IV pole or through a hard wired connection.

4. Direct connection. The transmitter (interrogator) 72 in the controller 58 could send a signal to the panel 40 using the IV pole 42 as a conduit. However, this may eliminate the possibility of multiplexing signals.

Different options exist for panel 40 power. In one example, the entire panel and all of its components may be powered with a battery or set of batteries (not shown) located within the panel. The battery would power all RFID readers 48 and vibration devices 50 and could be easily replaced. In more detailed aspects, the panel may include a battery strength or "life remaining" indicator (not shown). In a more advanced version, the battery indicator may indicate its remaining "run time." In another embodiment, the RFID readers are mounted to the panel so that they are easily replaceable and have their own internal power supply. In this case, the entire panel is not rendered non-operational if a battery on one RFID reader is exhausted. Vibration devices likewise may be mounted so as to be easily replaceable and may have their own built-in or internal power supply. If the battery of one vibration device is exhausted, the panel may still be kept in operation with three other vibration devices that have working batteries.

A preferred system is to provide an RFID reader antenna 72 in the controller 58 or infusion device 56 with a passive antenna 70 on the pole 42 located near the controller RFID reader antenna 72. The passive pole antenna would be hardwired to the RFID readers 48 in the panel 40 and to the vibration devices 50. The controller RFID reader would not only provide signals to the passive pole antenna but also the power necessary for the panel RFID readers to operate with the mounted medication containers so that the panel RFID readers can read the RFID tags of the containers. The controller RFID antenna would also provide enough power to the passive antenna to power all panel RFID readers and vibration devices.

Although the RFID interrogators 48 are shown in FIG. 4 as being mounted in the panel 40, they may in another embodiment be mounted in the hooks 46 of the panel and may read an RFID tag 52 mounted in the bag from their hook locations. The RFID tags may be placed on the bag at a different location than that shown in FIG. 4.

In another embodiment, information from the four panel RFID readers 48 can be multiplexed by a multiplexing device to allow the controller 58 to communicate with all the RFID readers, each of which have a unique identification. After the RFID readers are assigned or associated with the controller 58, the logic programmed into the controller would be able to pole or communicate with an individual RFID reader when necessary or communicate with all the RFID readers sequentially. Logic programmed into the controller 58 would differentiate each of four IV bags 26 hanging on the panel 40 based on signal strength of the RFID readers and vibrations produced by vibration devices as explained in detail below. If an IV bag were placed on the panel in the channel "A" position 44A and the door 74 of the channel B pump module 56 were opened, the controller would alert the clinician through the display 76 and perhaps audibly.

However, it would be of benefit to have the interrogator panel 40 be passive (not powered), and not attached directly (wired) to the controller 58. If the antenna panel is attached to the controller, there would be a risk that a clinician may break the connection when removing the controller from the pole 42. It is therefore desirable to have a wireless or non-hardwired connection between the controller and the interrogator panel.

The infusion system in FIG. 4 comprises a controller 58, three infusion pump modules 56, and an RFID reader module 78. Further details of the general configuration and operation of such a modular infusion system may be found in U.S. Pat. No. 5,713,856 to Eggers entitled "Modular Patent Care System" incorporated herein by reference.

Figure 5:
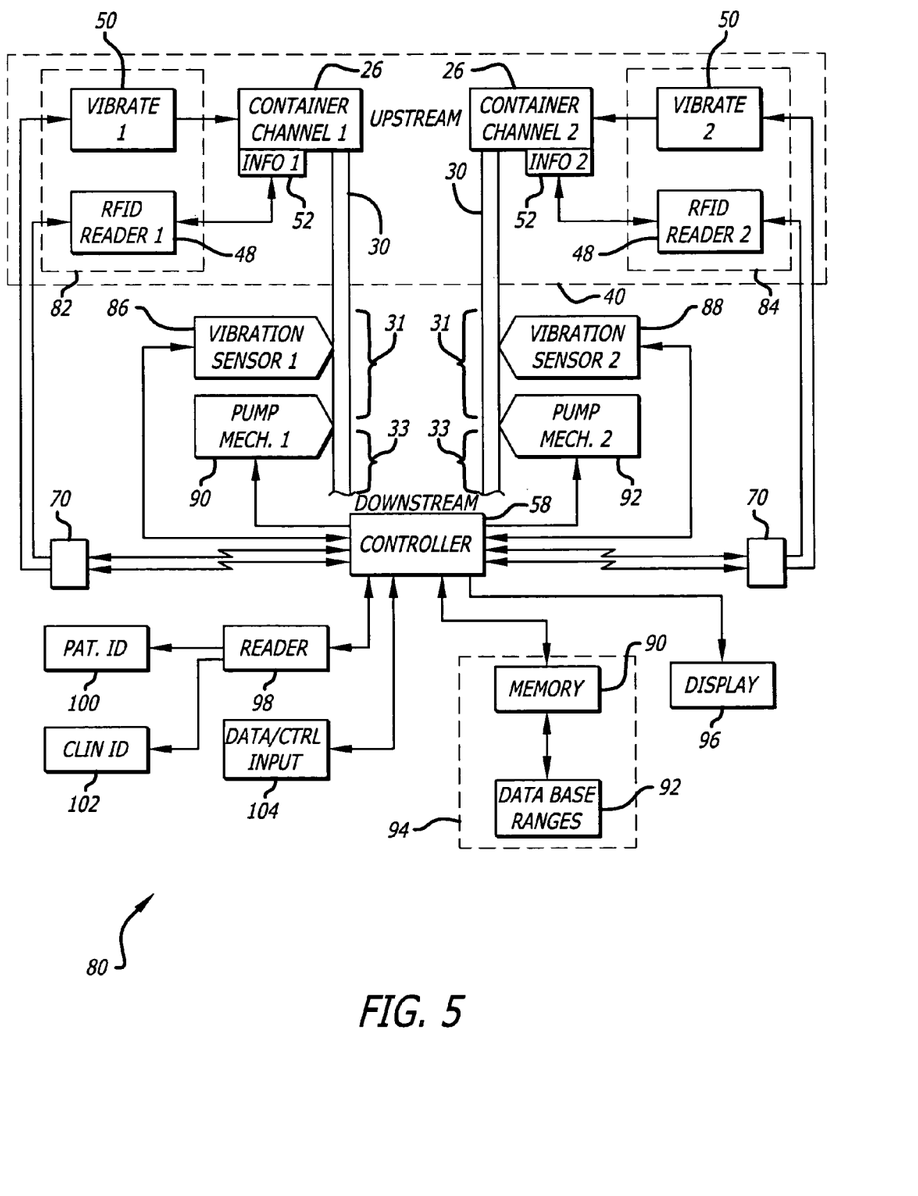
FIG. 5 is a diagrammatic view of a medication delivery system incorporating the components and system of FIG. 4 along with a memory with which the controller is connected, the memory storing a medication library having acceptable ranges of medication delivery parameters, the controller comparing the medication delivery information read from the RFID tag on the medication container to the acceptable medication delivery ranges of the medication library and providing an alert on a display if the selected delivery parameter is out of range

Referring now to FIG. 5, a block diagram of a medication safety system 80 featuring a multiplexed RFID interrogator panel 40 in accordance with aspects of the invention is shown. In the diagram, a channel 1 segment 82 of a panel is shown as is a channel 2 segment 84. A "container channel 1" 26 and "container channel 2" 26 are shown hung at the panel. Each segment and each container has an RFID reader 48 and a vibration device 50. The block showing the containers also shows that each container has an information device 52 which in one embodiment, is an RFID tag programmed with certain medication information. Downstream of each container is located a vibration sensor 86 and 88 and a pump mechanism 90 and 92. The vibration sensor may comprise a pressure transducer adapted to convert pressure changes in fluid within the conduit 30 to electrical signals. Such pressure changes may arise from a variety of conditions, such as when the volume of fluid in the medication container decreases over a period of time. In some cases, the pressure changes occur more rapidly or over a shorter period of time, such as when the medication container is lowered or moved. In addition, the pressure changes may be cyclical and occur even more rapidly, such as when the vibration device is vibrating the fluid in the container. In any case, the conduit 30 or IV tubing acts as a conduit for transmitting these pressure changes to the pressure transducer in the infusion pumping module 56. The transducer transmits electrical signals representative of the pressure changes to the controller 58.

It is to be understood that the term "vibration device" is used for ease of reference and is meant to encompass devices that, upon command from the controller 58, produces pressure disturbances or changes in fluid. The vibration device is adapted and located so as to produce pressure disturbances having a frequency and sufficient strength or energy to propagate to the vibration sensors of a medication delivery apparatus. A frequency of about 20 Hz is preferred, although lower and higher frequencies may be used. It is not intended that the vibration device be limited to devices having a mechanically vibrating element that contacts the container 26 or conduit 30. In addition, although in FIG. 4 the vibration device 50 is located adjacent the container 26, the vibration device in another embodiment not shown may be located adjacent to or coupled to the conduit 30 extending from the container 26.

It is also to be understood that the terms "upstream" and "downstream" designate a frame of reference along the conduit 30, as indicated in FIG. 5. An upstream element on the conduit is closer to the container 26 than a downstream element on the conduit. Conversely, the downstream element is closer to the patient than the upstream element. Within a flow control apparatus, such as the infusion pump module 56, there is an upstream portion 31 and a downstream portion 33. The upstream portion 31 of the flow control apparatus begins at the point where the conduit enters the apparatus from the container and ends near the point where a flow control device, such as a valve or the pump mechanism 90, 92, is located within the apparatus. The downstream portion 33 of the flow control apparatus begins near the point where the flow control device is located and ends at the point where the conduit exits the apparatus toward the patient. As shown in FIG. 5, the vibration sensors 86, 88 or upstream pressure sensors are coupled to the respective conduits 30 at upstream portions 31. Downstream pressure sensors (not shown) may be coupled to the conduit at the downstream portions in enable detection of an occlusion of the conduit, or other fluid delivery problems, occurring beyond the point where the conduit exits the infusion pump module.

The panel RFID readers 48 and vibrators 50 are wired to a passive antenna 70 (shown in two parts for ease in illustration). In this case, they are hard-wired, but in another case may be wirelessly connected. The controller 58 which controls the operation of the pump mechanisms 90 and 92, and receives signals from the downstream vibration sensors 86 and 88, also communicates with the passive antenna 70, in this case wirelessly. Therefore a communication pathway exists between the controller and each RFID reader 48 on the panel 40 and between the controller and each vibration device 50 on the panel. In another embodiment, there may not be a direct communication path between the controller and each vibration device, but instead, the vibration device may be activated by other means, such as by activation of the RFID reader 48 on the same panel segment 82.

The controller 58 is also connected to a memory 90 in which, or associated with which, is a data base 92 of ranges of acceptable medication delivery parameters. The memory and/or data base may be local to the controller or may be remotely located. In one embodiment, the memory and data base take the form of a drug library 94. For further details and information concerning an example of a drug library, see U.S. Pat. No. 5,681,285 to Ford, incorporated herein by reference. Upon obtaining the information from the information device 52 of each container 26, the controller will compare it to the data base to determine if the delivery parameters of the information device fall within acceptable ranges in the data base. If so, the controller may then automatically program the respective pump with those parameters. If the parameters fall outside of a "soft" range or limit, the controller may provide a visual alert on a display 96 and also an audible alert. The controller may permit the clinician to override the violation of a soft limit and proceed with the infusion. If a medication delivery parameter falls outside a "hard" range or limit, the controller would also provide a visual and audible alert, but may not permit the clinician to override the limit. The above process of obtaining the information from the information device, comparing the information to the data base, and providing an alert is performed under the command of a delivery parameter verification system.

The controller 58 is also connected, in this embodiment, to a reader 98 for reading the patient's identification device 100. By this means, the pump 56 associated with or controlled by the controller may be identified with a patient. Then the controller may check that all the containers 26 hung on the panel 40 are indeed for the patient identified with the respective pump. This adds an additional layer of safety in the automatic pump programming process. The reader 98 in this embodiment is also usable for identifying the clinician's identification device 102. Such information may be used for record keeping or may be used for controlling access to the pumps. The controller may compare the clinician identified by the reader 98 to a data base of authorized clinicians and if this clinician is not in the data base, the controller may not permit the infusion to go forward. The reader may take the form of a bar code reader, an RFID reader attached to the controller housing, as shown in FIG. 4, or other. In the case where a housing-mounted reader is used, it would permit the automatic acquisition of identification information without having to use a hand-held bar code scanner.

Also shown in FIG. 5 is a data and control input device 104 to the controller 58 which may take the form of a keypad, keyboard, or other device connected with the controller. This may be used by the clinician to override soft limits, and for various other uses.

Figure 6:
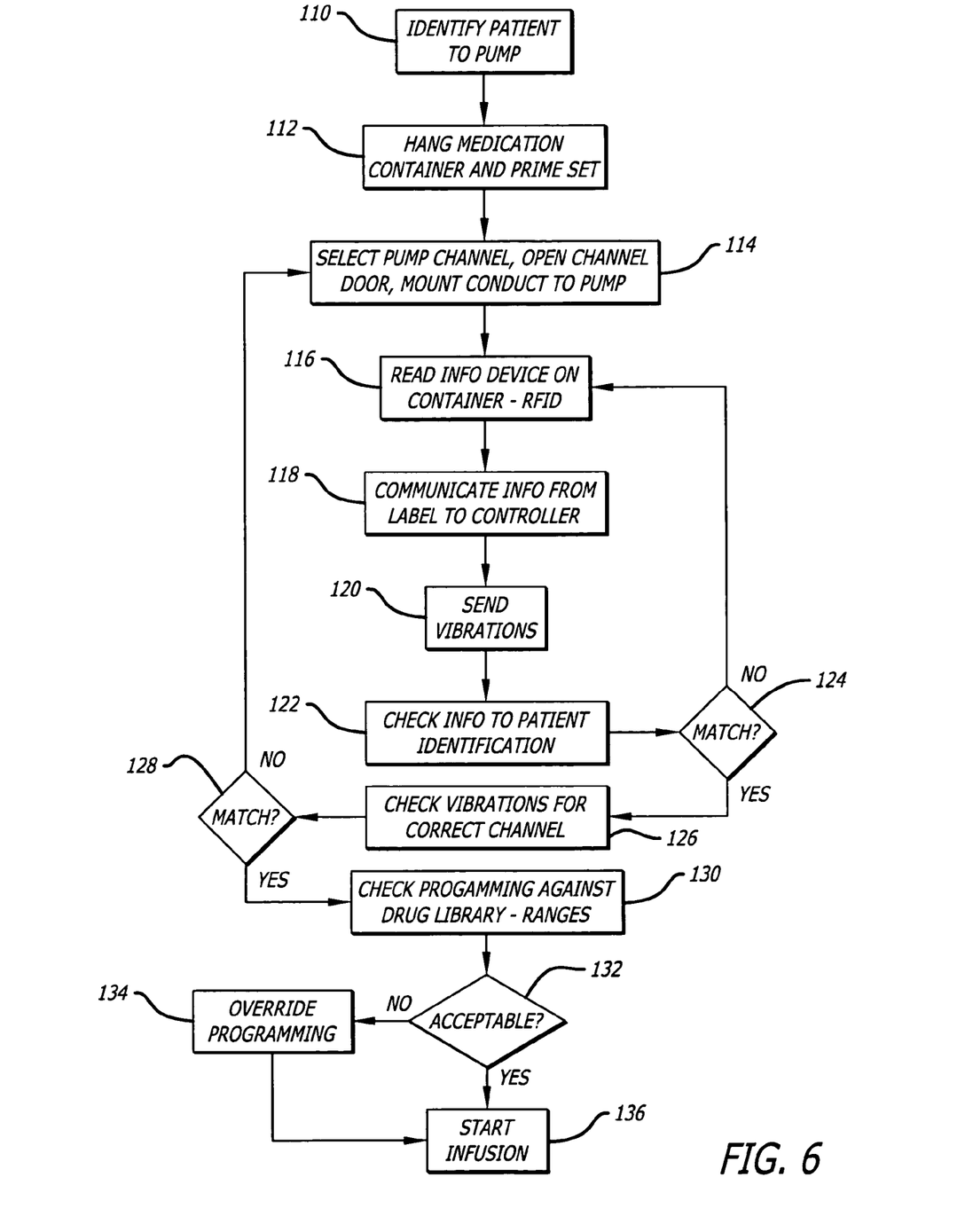
FIG. 6 is flow diagram of a method in accordance with aspects of the invention in which readers at a panel wirelessly read the information devices on medication containers, communicate the read information to a pump or controller of a pump, verify that the medication delivery parameters are within acceptable ranges, and automatically program the pump for infusion of the medication to a patient.

Referring now to the flow diagram of FIG. 6, an embodiment of the operation of a medication safety method featuring a multiplexed RFID interrogator panel is shown. In the first block 110, the patient is identified to the pump. Next, medication containers and associated fluid administration sets are hung and primed 112. In the case of a multi-channel pump, the door of one of the pump channels is opened 114 which thereby selects the pump as the active device at that time for programming. The panel 40 (FIG. 4) RFID reader 48 at the panel associated with that pump channel (such as segment 44A of the panel is associated with channel A of a pump) is activated to read the information device 116 on the medication container. The medication delivery information read from the RFID tag (information device) 52 on the container 26 is then communicated 118 to the controller 58. The associated vibration device 50 on the panel 40 is then activated to cause mechanical vibrations 120 in the medical fluid in the container. The patient identification is checked 122 and if incorrect 124, the medication must be checked again 116. At the same time, the vibration sensor 86 or upstream pressure sensor at the pump channel is monitored to determine if vibrations exist 126 in the conduit 30 mounted in that channel. If no vibrations are detected 128, the clinician is advised of such and the conduit from the container must be moved to the correct pump channel 114.

The controller checks the medication delivery parameters obtained from the medication container against a data base of acceptable ranges and parameters 130. If not acceptable 132, the possibility of programming override 134 may exist. If the parameters are acceptable, the infusion may be started 136 by the clinician pressing the START key. A START key can be seen and is described more fully in U.S. Pat. No. 5,713,856 to Eggers entitled "Modular Patent Care System" incorporated herein by reference.

In another embodiment, the clinician may also be required to use his/her employee badge 102 (FIG. 5) or other personal device (containing an RFID transponder) to identify himself/herself to the infusion system 80 by placing it in proximity to the controller 58 within which is located an RFID interrogator/reader (not shown).

When a secondary container of medical fluid needs to be administered to a patient, the clinician would lower the primary container by hanging it from a small hook (not shown) attached to the bottom of the panel 40. The secondary container would be hung in place of the primary container, and the conduit of the secondary container would be connected to a port, such as a Y-site connector, on the conduit of the primary container. Preferably, the port is located between the primary container and the infusion device 56. In this way, fluid from the secondary container would be delivered to the patient through the conduit of the primary container. The system would recognize the secondary container being put in place of the primary container and program the infusion to be at a secondary rate. The secondary container is recognized by the RFID interrogator 48 after a change in pressure upstream from the infusion device is sensed by the vibration sensor 86 or upstream pressure sensor, or by periodic polling or reading of RFID tags that exist within range of the RFID interrogator. Completion of the secondary infusion can be signaled at least in part by a recognizable rate or pattern of pressure change that occurs after the secondary container becomes empty. When the secondary infusion is completed, the controller would change to the primary rate and notify the clinician to place the primary container in it original position.

The system and method in accordance with the invention accomplishes the programming of an infusion pump in a passive way and provides a medication safety system by verifying that the right drug is given to the right patient at the right time with correct dose and infusion rate.

The term "controller" as used herein is meant to refer to a programming unit that can be used to control the operation of a pump system, such as that in the Medley® patient care system distributed by ALARIS Products of Cardinal Health, San Diego, Calif. mentioned above. However, it may also refer to the programming of a single pump such as the Signature Edition® pump also distributed by ALARIS Products of Cardinal Health, San Diego, Calif., as appropriate, or other medical instrument that may be programmed to introduce fluids to a patient. The system in accordance with the present invention could be used in connection with the Medley patient care system and the Signature Edition infusion system to provide a facilitative medication system at the bedside. Infusion setup would be automatic with this system with the clinician only needing to verify the setup by pushing the START key on the pump or controller 56 as the case may be. Infusion safety would be improved by verifying that the right drug is given to the right patient at the right time with the correct dose and infusion rate.

The panel 40 shown in FIGS. 2, 3, and 4 may be attached to the pole 42 by means of a standard pole clamp (not shown) used in the medical field. For example, a pole clamp such as that shown in FIG. 3 of U.S. Pat. No. 6,593,528, is usable for such a purpose. The pole clamp may be permanently mounted to the back of the panel and is tightly secured to a pole when use of the panel is needed. This permits mobility of the panels. In another case where standard poles are needed, the panel may be easily mounted to such standard poles.

In another embodiment, the back of the panel 40 may have two or more pole clamps spaced laterally apart. Preferably, a pole clamp is placed at three different locations on the panel, center, left, and right, so that the panel could be offset when two controllers 58 are used. Multiple pole clamps provide for more versatility in placement and organization. For example, a pair of infusion pump modules 56 mounted on the left side of a first controller 58 can be used with a first panel 40 mounted so as to be offset to the left. A second pair of infusion pump modules 56 mounted on the right side of a second controller 58, which is mounted below the first controller, can be used with a second panel 40 mounted below the first panel and offset to the right side. In this way, containers and conduits for the first pair of infusion pumps are kept separate from containers and conduits for the second pair of infusion pump modules, thereby eliminating conduit cross-over errors.

Syringes may also have RFID labels and may be read directly from an RFID interrogator mounted in a syringe module in the modular infusion system. The syringe adapter could have an incorporated interrogator which would connect with the system when attached.

From the foregoing, it will be appreciated that the system and method in accordance with the principles of the invention provide effective means to determine that a fluid supply is correctly connected to an infusion pump in order to ensure infusion of the proper drug.

What is claimed is:

1. A medication safety system for reading medication delivery information from an information device located at a medication container and providing that medication delivery information to a medication delivery apparatus, the system comprising:

a panel at which the medication container having the information device is mounted, the panel comprising a vibration device configured to impart vibrations to the medication of the container;

a conduit connected to the medication container configured to conduct the medication of the container to the medication delivery apparatus;

a reader located at the panel configured to wirelessly read the information device and to provide an information signal representative of the information contained in the information device;

a vibration sensor located at the medication delivery apparatus, the vibration sensor configured to detect vibrations in the medication of the conduit and provide a vibration signal when vibrations are sensed; and a controller located at the medication delivery apparatus coupled to the reader, the vibration sensor, and the vibration device, the controller configured to receive the information signal and the vibration signal, to activate the vibration device, and to configure the medication delivery apparatus in accordance with the information signal.

2. The medication safety system of claim 1 wherein:

the information device comprises patient identification information and an infusion pump programming parameter; and the controller is further adapted to compare the patient identification information to information from a patient to which the medication delivery apparatus has been identified, and to automatically program the mediation delivery apparatus with the pump programming parameter.

3. The medication safety system of claim 1 wherein the controller is configured to receive the information signal wirelessly.

4. The medication safety system of claim 1 wherein the wireless reader comprises an RFID interrogator that reads the information device on the medication container.

5. The medication safety system of claim 1 wherein the panel comprises:

multiple locations at which a plurality of medication containers may be mounted, each container having a conduit configured to conduct the medication of the respective container to the medication delivery apparatus and each container having an information device providing medication delivery information and patient identification information; and at least one wireless information reader device located at the panel so as to read information contained in each of the information devices mounted at the panel.

6. The medication safety system of claim 5 further comprising a multiplexing device that provides multiplexed multiple information signals representative of the information contained in each of the information devices.

7. The medication safety system of claim 5 comprising a plurality of wireless information reader devices located at the panel so as to read information contained in respective information devices mounted at the panel adjacent the respective reader device.

8. The medication safety system of claim 7 wherein the information reader devices comprise RFID readers.

9. The medication safety system of claim 5 wherein the controller compares the patient identification information for each of the containers to a patient identified to the pump and if the identifications do not match, the controller provides an alert.

10. The medication safety system of claim 1 further comprising a delivery parameter verification system in which the delivery parameter read from the information device is compared to a data base having an acceptable range for the delivery parameter and if the delivery parameter contained in the information signal is outside the acceptable range, the verification system will provide an alert.

11. The medication safety system of claim 10 wherein the acceptable range of the data base comprises a hard limit and a soft limit, the verification system disabling the pump from operation if the delivery parameter from the information signal exceeds the hard limit and not disabling the pump from operation but providing an alert if the delivery parameter from the information signal exceeds the soft limit but does not equal or exceed the hard limit.

12. The medication safety system of claim 10 wherein the verification system is located within the controller.

13. The medication safety system of claim 10 wherein the verification system is located at a location remote from the controller.

14. The medication safety system of claim 1 further comprising a patient identification reader configured to wirelessly read identification information of a patient and communicate the patient identification information to the controller.

15. The medication safety system of claim 1 further comprising a clinician identification reader configured to wirelessly read identification information of a clinician and communicate the clinician identification information to the controller.

16. The medication safety system of claim 1 further comprising:
an IV pole to which the panel is mounted and to which the medication delivery apparatus and controller are mounted; and
a receiver mounted at the pole adjacent the controller, the receiver configured to conduct information signals from the medication reader to the controller.

17. The medication safety system of claim 1 wherein:
the controller is further configured to provide an alert if it does not receive the vibration signal when the information device of the same medication container is read by the panel.

18. The medication safety system of claim 17 wherein the vibration sensor comprises a pressure transducer coupled to the conduit at an upstream portion of the delivery apparatus and adapted to convert changes in pressure in the medication of the conduit to an electrical signal.

19. A medication safety method for reading medication delivery information from an information device located at a medication container and providing that medication delivery information to a medication delivery apparatus, the method comprising:
mounting the medication container having the information device to a panel disposed above the medication delivery apparatus;
wirelessly reading the information device with a reader mounted in the panel and providing an information signal representative of the information contained in the information device;
imparting vibrations to the medication contained in the container at the panel;
sensing vibrations in the medication at the medication delivery apparatus; and
receiving the information signal and configuring the medication delivery apparatus in accordance with the information signal.

20. The medication safety method of claim 19 further comprising:
reading patient identification information and an infusion pump programming parameter from the information device;
comparing the patient identification information from the information device to information from a patient to which the medication delivery apparatus has been identified; and
automatically program the medication delivery apparatus with the pump programming parameter.

21. The medication safety method of claim 19 wherein the step of receiving the information signal and configuring the medication delivery apparatus in accordance with the information signal is performed wirelessly.

22. The medication safety method of claim 19 wherein the step of wirelessly reading the information device is performed with RF energy.

23. The medication safety method of claim 19 further comprising:
mounting multiple medication containers to the panel, each medication container having a respective information device; and
wirelessly reading each of the information devices with at least one reader mounted in the panel and providing information signals representative of the information contained in each of the information devices.

24. The medication safety method of claim 23 further comprising multiplexing the multiple information signals representative of the information contained in each of the information devices.

25. The medication safety method of claim 23 comprising:
wirelessly reading each of the plurality of information devices with multiple readers mounted in the panel and providing a plurality of information signals representative of the information contained in each of the information devices; and
multiplexing the multiple information signals representative of the information contained in each of the information devices.

26. The medication safety method of claim 23 further comprising:
comparing the patient identification information for each of the containers to a patient identified to the pump; and
if the identifications do not match, providing an alert.

27. The medication safety method of claim 19 further comprising:
comparing the delivery parameter read from the information device to a data base having an acceptable range for the delivery parameter; and
if the delivery parameter contained in the information signal is outside the acceptable range, providing an alert.

28. The medication safety method of claim 27 wherein the step of comparing further includes comparing the delivery parameter read from the information device to a data base having an acceptable range in which there is a hard limit and a soft limit;
disabling the operation of the pump if the delivery parameter from the information signal exceeds the hard limit; and
providing an alert if the delivery parameter from the information signal exceeds the soft limit but does not equal or exceed the hard limit and not disabling the pump from operation.

29. The medication safety method of claim 27 wherein the comparing step is performed at a controller of the medication delivery apparatus.

30. The medication safety method of claim 27 wherein the comparing step is performed at a location remote from the medication delivery apparatus.

31. The medication safety method of claim 19 further comprising wirelessly reading identification information of a patient and communicate the patient identification information to the medication delivery apparatus.

32. The medication safety method of claim 19 further comprising wirelessly reading identification information of a clinician and communicating the clinician identification information to the medication delivery apparatus.

33. The medication safety method of claim 19 further comprising: mounting the panel and the medication delivery apparatus to an IV pole; mounting a receiver at the pole adjacent the medication delivery apparatus; and conducting information signals from the medication reader to the controller.

34. The medication safety method of claim 19 further comprising:
providing an alert if vibrations are not sensed when the information device of the same medication container is read at the panel.

35. The medication safety method of claim 19 further comprising:
imparting pressure disturbances to the medication contained in the container at the panel; sensing pressure disturbances in the medication at the medication delivery apparatus; and providing an alert if pressure disturbances are not sensed when the information device of the same medication container is read at the panel.

* * * * *